US00PP15496P2

(12) United States Plant Patent
Slaughter et al.

(10) Patent No.: US PP15,496 P2
(45) Date of Patent: Jan. 25, 2005

(54) PEACH TREE NAMED 'CALARA'

(50) Latin Name: *Prunus persica*
Varietal Denomination: Calara

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 5 days.

(21) Appl. No.: 10/724,591

(22) Filed: Nov. 25, 2003

(51) Int. Cl.[7] ..... A01H 5/00
(52) U.S. Cl. ..... Plt./197
(58) Field of Search ..... Plt./197

(56) References Cited

PUBLICATIONS

UPOV–ROM GTITM Computer Database, 2003/06, GTI Jouve Retrieval Software, citation for 'Lara'.*

* cited by examiner

*Primary Examiner*—Bruce R. Campell
*Assistant Examiner*—S B McCormick-Ewoldt
(74) *Attorney, Agent, or Firm*—Wells St. John P.S.

(57) ABSTRACT

A new and distinct variety of peach tree (*Prunus persica*), and which is denominated varietally as 'Calara', and which produces an attractively colored yellow-fleshed, clingstone peach which is mature for harvesting approximately October 1 to October 12 under ecological conditions prevailing in the San Joaquin Valley of central California.

1 Drawing Sheet

BACKGROUND OF THE NEW VARIETY

The present invention relates to a new, novel and distinct variety of peach tree, *Prunus persica,* which has been denominated varietally as 'Calara'.

The present variety of peach tree resulted from an ongoing program of fruit and nut tree breeding. The purpose of this program is to improve the commercial quality of deciduous fruit and nut varieties, and rootstocks, by creating and releasing promising selections of *prunus, malus* and *regia* species. To this end we make both controlled and hybrid cross pollinations each year in order to produce seedling populations from which improved progenies are evaluated and selected.

The seedling 'Calara' was originated by us from a population of seedlings grown in our experimental orchards located near Fowler, Calif. The seedlings, grown on their own roots, were the result of a controlled cross of the yellow-fleshed freestone peach tree 'Fayette' (nonpatented), which was used as the pollen parent, and a late ripening, yellow-fleshed, clingstone peach tree, of known parentage (unpatented), which was used as the seed parent. One seedling, C10.060, which is the present variety, exhibited especially desirable characteristics and was marked for subsequent observation. After the 1997 fruiting season, the new variety of peach tree was selected for advanced evaluation and repropagation.

ASEXUAL REPRODUCTION

Asexual reproduction of this new and distinct variety of peach tree was accomplished by budding the new peach tree to 'Nemaguard' Rootstock (non-patented). This was performed by us in our experimental orchard located near Fowler, Calif. Subsequent evaluations have shown those asexual reproductions run true to the original tree. All characteristics of the original tree, and its fruit, were established and appear to be transmitted through succeeding asexual propagations.

SUMMARY OF THE VARIETY

'CALARA' is a new and distinct variety of peach tree, which is of large size, and which has vigorous growth. This new peach tree is also a regular and productive bearer of relatively large, firm, yellow fleshed, clingstone fruit which have good flavor and eating qualities. This new tree has a medium chilling requirement of approximately 700 hours, and further produces relatively uniformly sized fruit throughout the tree. The fruit produced by this new variety has a non-melting flesh which makes it ideal for storage. In addition, the fruit also appears to have good handling and shipping qualities. 'Calara' is most closely similar to the Autumn Lady Peach Tree (U.S. Plant Pat. No. 4,398). However, it is distinguishable therefrom by ripening some 5–10 days later than the Autumn Lady Peach Tree when grown at the same geographical location. Still further, the 'Calara' peach tree bears fruit which are ripe for commercial harvesting and shipment on approximately October 1 to October 12 under the ecological conditions prevailing in the San Joaquin Valley of central California. In relative comparison to the seed parent of the new variety, the present peach tree bears fruit 38 or more days later at the same geographical location. In comparison to the female patent 'Calara' is more oblate in shape and exhibits a 40% to about 60% reddish blush. The female parent on the other hand is more elongated in shape and typically expresses about 10% to about 25% reddish blush over the fruit surface.

BRIEF DESCRIPTION OF THE DRAWING

The accompanying drawing which is provided is a color photograph of the present variety. It depicts two whole mature fruit, and one fruit dissected substantially in the equatorial plane, and which reveals the flesh and the stone characteristics thereof. The external coloration of the fruit as shown is sufficiently matured for harvesting and shipment. Additionally, the photograph displays a sample vegetative shoot bearing typical leaves, and a typical stone, with the flesh removed. The colors in this photograph are as nearly true as is reasonably possible in a color representation of this type. Due to chemical development, processing and printing, the leaves and fruit depicted in these photographs may or may not be accurate when compared to the actual specimen. For this reason, future color references should be made to the color plates (Royal Horticultural Society) and descriptions provided hereinafter.

DETAILED DESCRIPTION

Referring more specifically to the pomological details of this new and distinct variety of peach tree, the following has been observed during the seventh fruiting season under the ecological conditions prevailing at orchards which are located near the town of Fowler, county of Fresno, state of California. All major color code designations are by reference to The R.H.S. Colour Chart (Fourth Edition) and which is provided by The Royal Horticultural Society of Great Britain. Common color names are also occasionally used.

Tree:

*Size.*—Generally — Considered medium-large as compared to other common commercial peach cultivars ripening in the late season of maturity. The tree of the present variety was pruned to a height of approximately 320.0 cm to about 325.0 cm at maturity.

*Vigor.*—Considered moderately vigorous. The present peach tree variety grew from about 134.0 cm to about 150.0 cm in height during the first growing season. The new variety was pruned to a height of approximately 128.0 cm in the first dormant season and primary scaffolds were then selected for desired tree structure.

*Productivity.*—Productive. Fruit set varies from 1.5 to several times more than the desired crop load. Fruit set is spaced by thinning to develop the remaining fruit into desired market size fruit. The number of the fruit set varies with prevailing climatic conditions, and cultural practices employed during the bloom period and is therefore not distinctive of the variety. In comparison to the Autumn Lady Peach Tree (U.S. Plant Pat. No. 4,398) the fruit set is greater and achieves economic production levels not typically experienced with the Autumn Lady Peach Tree.

*Bearer.*—Regular. Fruit set has been heavy during the years of observation and thinning was necessary during the past 5 years.

*Form.*—Upright, and pruned to a vase shape.

*Density.*—Considered medium dense. It has been discovered that pruning the branches from the center of the tree to obtain a resulting vase shape allows for air movement and appropriate amounts of sunlight to enhance fruit color and renewal of fruiting wood throughout the tree.

*Hardiness.*—The present tree was grown and evaluated in USDA Hardiness Zone 9. Winter chilling requirements of the new tree are approximately 700 hours below 7.0 degrees C. The variety appears to be hardy under typical Central San Joaquin Valley conditions.

Trunk:

*Diameter.*—Approximately 14.0 cm in diameter when measured at a distance of approximately 15.24 cm above the soil level. The measurement was taken at the end of the sixth growing season.

*Bark texture.*—Considered moderately rough, with numerous folds of papery scarfskin being present.

*Lenticels.*—Numerous flat, oval lenticels are present. The lenticels range in size in size from approximately 4.0 to about 7.0 millimeters in width, and from 1.0 to about 3.0 millimeters in height.

*Lenticel color.*—Considered an orange brown, (RHS Greyed-Orange Group N170 A).

*Bark coloration.*—Variable, but it is generally considered to be a medium grey-brown, (RHS Greyed-Orange Group 166 A).

Branches:

*Size.*—Considered medium for the variety.

*Diameter.*—Average as compared to other peach varieties. The branches have a diameter of about 6.5 centimeters when measured during the seventh year after grafting.

*Surface texture.*—Average, and appearing furrowed on wood which is several years old.

*Crotch angles.*—Primary branches are considered variable and are between about 45 to 52 degrees when measured from the horizontal axis. This particular characteristic is not considered distinctive of the variety, however.

*Current season shoots.*—Surface texture — Substantially glabrous.

*Internode length.*—Approximately 2.4 to about 2.6 cm.

*Color of mature branches.*—Medium brown, (RHS Greyed-Orange 177 B).

*Current seasons shoots.*—Color — Light green, (RHS Yellow-Green Group 147 C). The color of new shoot tips is considered a bright and shiny green (RHS Yellow-Green Group 144 B).

Leaves:

*Size.*—Considered medium large for the species. Leaf measurements have been taken from vigorous, upright, current-season growth at approximately mid-shoot.

*Leaf length.*—Approximately 152.0 to about 158.0 millimeters.

*Leaf width.*—Approximately 42.0 to about 45.0 millimeters.

*Leaf base shape.*—Slightly oblique relative to the leaf longitudinal axis.

*Leaf form.*—Lancelolate.

*Leaf tip form.*—Acuminate.

*Leaf color.*—Upper Leaf Surface — Dark green, (approximately RHS Yellow-Green Group 147 A).

*Leaf texture.*—Glabrous.

*Leaf color.*—Lower Surface — Medium green, (RHS Yellow-Green Group 148 B).

*Leaf venation.*—Pinnately veined.

*Mid-vein.*—Color — Light yellow green, (RHS Yellow-Green Group 151 D).

*Leaf margins.*—Slightly undulating. Form — Considered crenate. Occasionally doubly so. Uniformity — Considered generally uniform.

*Leaf petioles.*—Size — Considered medium. Length — About 8.0 to about 11.5 mm. Diameter — About 1.5 to about 2.0 mm. Color — Pale green, (RHS Yellow-Green Group 151 A).

*Leaf glands.*—Size — Considered medium. Approximately 1.5 mm in length, and about 1.0 mm in height. Number — Generally one gland per margin side. Occasionally two glands per margin side. Type — Reniform. Color — Considered a pale orange (RHS Orange-Red Group 31B).

*Leaf stipules.*—Size — Medium large for the variety. Number — Typically 2 per leaf bud and up to 6 per shoot tip. Form — Lanceolate in form and having a serrated margin. Color — Green, (RHS Yellow-Green Group 144 A) when young, but graduating to a brown color, (RHS Grey-Orange group 166 B) with advancing senescence. The stipules are considered to be early deciduous.

Flowers:

*Flower buds.*—Generally — The floral buds, depending on the stage of development, are approximately 7.0 millimeters wide; about 11.0 millimeters long; conic in form; and slightly appressed relative to the bearing shoot.

*Flower buds.*—Color — This characteristic is dependent upon the proximity to bloom. The bud scales are deep purple, (approximately RHS Greyed-Purple Group N186 B). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress, and therefore this information is not available.

*Date of first bloom.*—Mar. 4, 2002.

*Blooming time.*—Considered mid-season in relative comparison to other commercial peach cultivars grown in the central San Joaquin Valley. The date of full bloom was observed on Mar. 9, 2002. The date of bloom varies slightly with climatic conditions and cultural practices.

*Duration of bloom.*—Approximately 9 days. This characteristic varies slightly with the prevailing climatic conditions.

*Flower type.*—The variety is considered to have a showy type flower.

*Flower size.*—Flower diameter at full bloom is approximately 37.0 to about 43.0 millimeters.

*Bloom quantity.*—Considered abundant.

*Flower bud frequency.*—Normally 1 to 2 flower buds appear per node.

*Petal size.*—Generally — Considered medium for the species. Length — Approximately 17.0 to about 20.0 millimeters. Width — Approximately 16.0 to about 18.0 millimeters.

*Petal form.*—Slightly ovoid.

*Petal count.*—Nearly always 5.

*Petal texture.*—Glabrous.

*Petal color.*—Light pink, (RHS Red-Purple Group 62 B and darkening to a medium pink, (RHS Red-Purple Group N57 C).

*Fragrance.*—Slight.

*Petal claw.*—Form — The claw is considered generally ovoid and has a medium size when compared to other varieties. Length — Approximately 9.0 to about 11.0 millimeters. Width — Approximately 8.0 to about 10.0 millimeters.

*Petal margins.*—Generally considered variable, from nearly smooth to slightly ruffled, to moderately undulate.

*Petal apex.*—Generally — The petal apices generally appear slightly grooved at the tip.

*Flower pedicel.*—Length — Considered medium-long, and having an average length of approximately 3.0 to about 4.0 millimeters. Diameter — Considered average, approximately 2.0 millimeters. Color — A medium brown, (RHS Greyed-Orange Group 164 A).

*Floral nectaries.*—Color — A dull orange, (RHS Greyed-Orange Group N172 A).

*Calyx.*—Surface Texture — Generally glabrous. Color — Purple, (approximately RHS Greyed-Purple Group 187 B).

*Sepals.*—Surface Texture — The surface has a short, fine pubescent texture. Size — Average, and ovate in form. Color — A dull red, (approximately RHS Greyed-Purple Group 187 A).

*Anthers.*—Generally — Average in length. Color — Red to reddish-orange dorsally, (approximately RHS Greyed-Purple Group 187 C).

*Pollen production.*—Pollen is abundant, and has a yellow color, (approximately RHS Yellow-Orange Group 17 C).

*Filaments.*—Size — Length is variable, approximately 13.0 to about 16.0 millimeters long. Color — Considered light pink, (RHS Red Group 55 B).

*Pistil.*—Number — Usually 1, rarely 2. Generally — Average in size. Length — Approximately 16.0 to about 19.0 millimeters including the ovary. Color — Considered a very pale green, (approximately RHS Yellow-Green Group 150 B). Surface Texture — The variety has a long pubescent pistil.

Fruit:

*Maturity when described.*—Firm ripe condition (shipping ripe).

*Date of first picking.*—Oct. 1st, 2003. Date of last picking — Oct. 12, 2003. The date of harvest varies slightly with the prevailing climatic conditions.

*Size.*—Generally — Considered large, and uniform.

*Average cheek diameter.*—Approximately 72.0 to about 80.0 millimeters.

*Average axial diameter.*—Approximately 68.0 to about 74.0 millimeters.

*Typical weight.*—Approximately 277.0 grams. This characteristic is highly dependent upon the prevailing cultural practices, and therefore is not particularly distinctive of the variety.

*Fruit form.*—Generally — Considerably oblate. The fruit is generally uniform in symmetry.

*Fruit suture.*—Very shallow and smooth, extending from the base to the apex. No apparent callusing or stitching exists along the suture line.

*Suture.*—Color — This has a yellow background color, (approximately RHS Yellow-Orange Group 20 B).

*Ventral surface.*—Form — Only slightly indented.

*Apex.*—Rounded.

*Base.*—Generally retuse.

*Stem cavity.*—Generally elongated in the suture plane. Average depth of the stem cavity is about 8.0 mm. Average width of the stem cavity is about 12 mm.

*Fruit skin.*—Thickness — Considered medium in thickness, and tenacious to the flesh. Texture — Short, fine and pubescent. The pubescence is moderately abundant. Taste — Non-astringent. Tendency to crack — None observed.

*Color.*—Blush Color — This blush color is generally a faint red flecking on a minority of the skin of the fruit (approximately RHS Red Group 46 C), and generally is more present on the basal portions of the fruit. The blush covers approximately 40–60% of the fruit skin surface. The percentage of the blush on the fruit skin surface can vary and is generally dependant upon the prevailing conditions under which the fruit was grown.

*Ground color.*—Yellow orange, (approximately RHS Yellow-Orange Group 18 A).

*Fruit stem.*—Medium in length, approximately 5.0 to about 7.0 millimeters. Diameter — Approximately 2.0 to about 3.0 millimeters. Color — Pale yellow-green, (approximately RHS Yellow-Green Group 144 C).

*Flesh.*—Ripens — Evenly. Texture — Firm, juicy and dense. Considered non-melting. Fibers — Few, small, and tender ones are found. Aroma — Very slight. Eating Quality — Considered very good. Flavor — Considered sweet and mildly acidic. The flavor is considered both pleasant and balanced. Juice — Moderate. Brix — About 13.5 degrees. This characteristic varies slightly with the number of fruit per tree; prevailing cultural practices; and the surrounding climatic conditions. Flesh Code — Pale yellow-orange, (approximately RHS Yellow-Orange Group 23 C).

Stone:

*Type.*—Clingstone. This is in contrast to the closest variety known, Autumn Lady (U.S. Plant Pat. No. 4,398) which produces freestone fruit.

*Size.*—Considered medium for the variety. The stone size varies significantly depending on tree vigor, crop load and growing conditions.

*Length.*—Average, about 27.0 to about 31.0 millimeters.

*Width.*—Average, about 22.0 to about 24.0 millimeters.

*Diameter.*—Average, about 15.0 to 19.0 millimeters.

*Form.*—Obovoid.

*Base.*—The stone is usually rounded to slightly oblique to the ventral side.

*Apex.*—Shape — The stone apex is raised and has a reasonably prominent tip.

*Stone surface.*—Surface Texture — Irregularly furrowed toward the basal end. Pitting is abundant generally but is typically more noted on the lateral sides and toward the apex. Ridges — The surface texture is generally characterized by more prominent ridges along the ventral edges. Ventral Edge — Width — Considered medium, and having a dimension of approximately 3.0 to about 4.0 millimeters when measured at the mid-suture. Dorsal Edge — Shape — Full, lightly grooved, and having a reasonably smooth margin.

*Stone color.*—The color of the dry stone is generally considered a reddish brown, (approximately Greyed-Red Group RHS 181 A).

*Tendency to split.*—Splitting has rarely been noted.

*Kernel.*—Size — Kernel is considered medium-large. Form — Considered ovoid. Pellicle — Pubescent. Color — (RHS Greyed-Orange Group 167 A).

*Use.*—The subject variety 'Calara' is considered to be a peach tree of the late season maturity, and which produces fruit which are considered firm, attractively colored, and which are useful for both local and long distance shipping.

*Keeping quality.*—Excellent. Fruit has stored well up to 25 days after harvest at 1.0 degree Celsius.

*Shipping quality.*—Good. The fruit of the new peach variety showed minimal bruising of flesh or skin damage after being subjected to normal harvest and packing procedures.

*Resistance to insects and disease.*—No particular susceptibilities were noted. The present variety has not been tested to expose or detect any susceptibilities or resistances to any known plant and/or fruit diseases.

Although the new variety of peach tree possesses the described characteristics when grown under the ecological conditions prevailing near Fowler, Calif., in the Central part of the San Joaquin Valley of California, it should be understood that variations of the usual magnitude and characteristics incident to changes in growing conditions, fertilization, pruning, pest control and horticultural management are to be expected.

Having thus described and illustrated our new variety peach tree, what we claim is new and desire to secure by Plant Letters Patent is:

1. A new distinct variety of peach tree substantially as illustrated and described, and which is characterized principally as to novelty by producing an attractively colored yellow-fleshed, clingstone peach which is mature for harvesting approximately October 1 to October 12 under the ecological conditions prevailing in the San Joaquin Valley of central California.

* * * * *

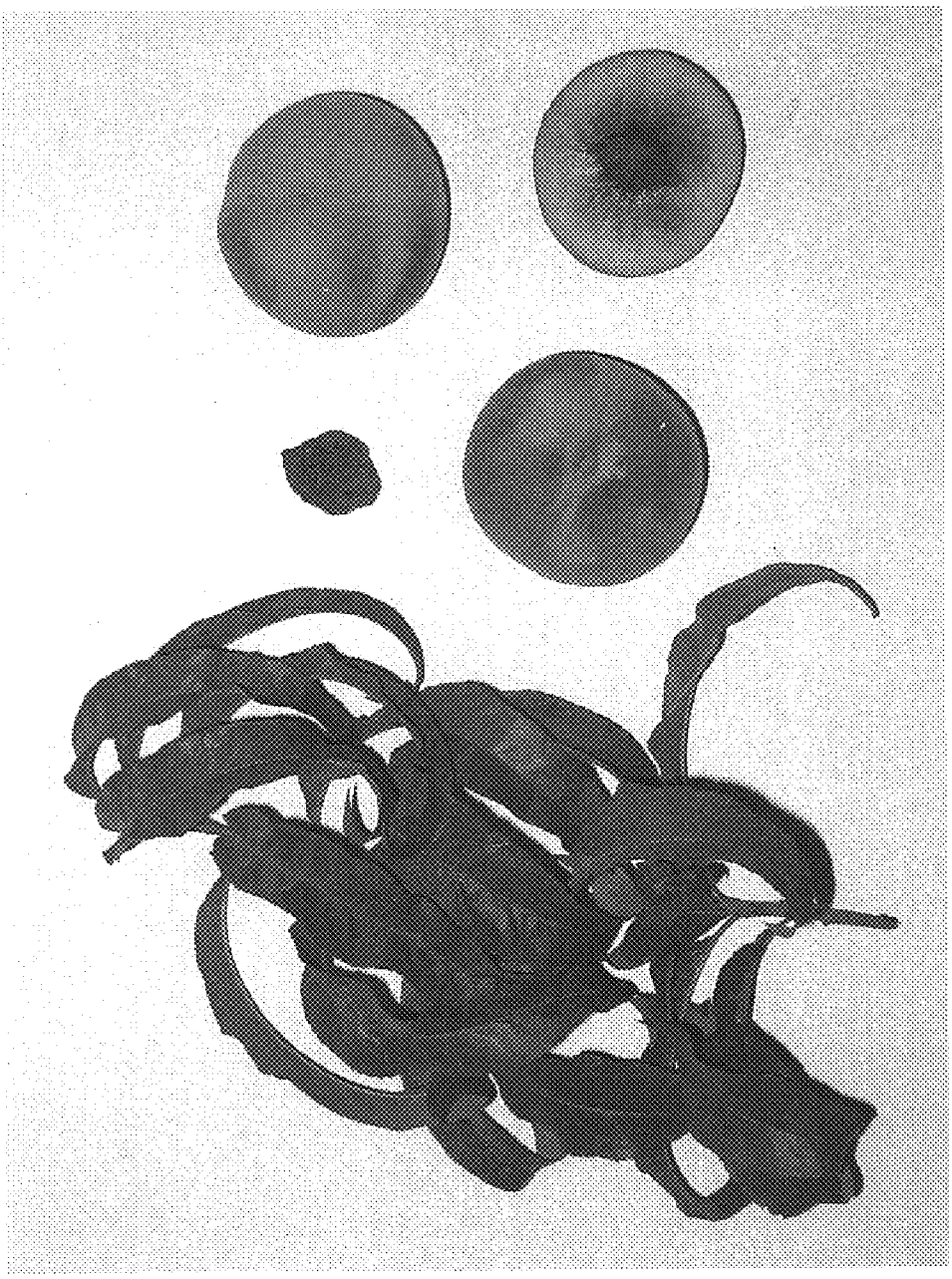

UNITED STATES PATENT AND TRADEMARK OFFICE

CERTIFICATE OF CORRECTION

PATENT NO. : PP 15,496 P2
DATED : January 25, 2005
INVENTOR(S) : John K. Slaughter et al.

It is certified that error appears in the above-identified patent and that said Letters Patent is hereby corrected as shown below:

Column 7,
Line 23, replace "Flesh Code" with -- Flesh Color --.

Signed and Sealed this

Nineteenth Day of July, 2005

JON W. DUDAS
*Director of the United States Patent and Trademark Office*